US006485755B1

(12) United States Patent
Antelman

(10) Patent No.: US 6,485,755 B1
(45) Date of Patent: Nov. 26, 2002

(54) METHODS OF USING ELECTRON ACTIVE COMPOUNDS FOR MANAGING CANCER

(75) Inventor: Marvin S. Antelman, Rehovot (IL)

(73) Assignee: Marantech Holding, Providence, RI (US)

(*) Notice: Subject to any disclaimer, the term of this patent is extended or adjusted under 35 U.S.C. 154(b) by 0 days.

(21) Appl. No.: 09/692,488

(22) Filed: Oct. 20, 2000

Related U.S. Application Data

(63) Continuation-in-part of application No. 09/552,172, filed on Apr. 18, 2000, now Pat. No. 6,258,385.
(60) Provisional application No. 60/174,793, filed on Jan. 6, 2000, provisional application No. 60/184,053, filed on Feb. 22, 2000, and provisional application No. 60/214,503, filed on Jun. 28, 2000.

(51) Int. Cl.$^7$ .................. A61K 33/38; A61K 33/00; A61K 47/00; A61K 47/30
(52) U.S. Cl. .................. 424/618; 424/600; 424/617; 424/635; 424/639; 424/646; 424/653; 424/630; 514/788.1
(58) Field of Search .................. 424/600, 617, 424/618, 630, 639, 646, 647, 648, 653, 635; 514/788.1

(56) References Cited

U.S. PATENT DOCUMENTS

| | | | |
|---|---|---|---|
| 3,923,982 A | 12/1975 | Lamand et al. .............. 424/140 |
| 4,447,254 A | 5/1984 | Hughes et al. .................. 71/67 |
| 4,574,782 A * | 3/1986 | Borrelli et al. ............... 600/10 |
| 4,735,796 A * | 4/1988 | Gordon ...................... 424/9.32 |
| 4,828,832 A | 5/1989 | De Cuellar et al. .......... 424/618 |
| 4,952,411 A | 8/1990 | Fox, Jr. et al. .............. 424/618 |
| 5,017,295 A | 5/1991 | Antelman .................... 210/764 |
| 5,073,382 A | 12/1991 | Antelman .................... 424/604 |
| 5,078,902 A | 1/1992 | Antelman .................... 210/764 |
| 5,089,275 A | 2/1992 | Antelman .................... 424/602 |
| 5,098,582 A | 3/1992 | Antelman .................... 210/759 |
| 5,211,855 A | 5/1993 | Antelman .................... 210/758 |
| 5,223,149 A | 6/1993 | Antelman .................... 210/764 |
| 5,320,906 A * | 6/1994 | Eley et al. ................. 428/402.2 |
| 5,334,588 A | 8/1994 | Fox, Jr. et al. .............. 514/171 |
| 5,336,416 A | 8/1994 | Antelman .................... 210/764 |
| 5,336,499 A | 8/1994 | Antelman .................... 424/405 |
| 5,571,520 A | 11/1996 | Antelman .................... 424/405 |
| 5,612,019 A | 3/1997 | Gordon et al. ............. 424/9.32 |
| 5,676,977 A | 10/1997 | Antelman .................... 424/618 |
| 5,772,896 A | 6/1998 | Denkewicz, Jr. et al. ... 210/754 |
| 5,928,958 A * | 7/1999 | Pilgrimm .................... 436/526 |

FOREIGN PATENT DOCUMENTS

JP   2000060976   2/2000

OTHER PUBLICATIONS

STN/CAS online, file CIN, Acc. No. 13(8):6866B, China Dly. (North Am. Ed.), Jan. 30, 1984, p. 5), Abstract.*
Antelman, Marvin S.; "Silver (II,III) Disinfectants"; *Soap/Cosmetics/Chemical Specialties*, Mar. 1994, pp. 52–59.
Antelman, Marvin S.; Abstracts of the American Chemical Society; 1992(203).
Antelman, Marvin S.; "Anti–Pathogenic Multivalent Silver Molecular Semiconductors"; *Precious Metals*; 1992(16); pp. 141–149.
Antelman, Marvin S.; "Multivalent Silver Bactericides"; *Precious Metals*; 1992(16); pp. 151–163.
Fung, Man C. and Bowen, Debra L.; "Silver Products for Medical Indications: Risk–Benefit Assessment", *Clinical Toxicology*, 1996, pp. 119–126.
Dorland et al., *Dorland's Illustrated Medical Dictionary*, Philadelphia: W.B. Saunders Company, 1994, 28$^{th}$ Edition, p. 351, 759, and 760.
Gennaro, A., Remington's Pharmaceutical Sciences, Easton, PA: Mack Publishing Company, 1985, 17$^{th}$ Edition, p. 1573–1575, 1585–1594, and 1601.

* cited by examiner

Primary Examiner—Jose' G. Dees
Assistant Examiner—Frank Choi
(74) Attorney, Agent, or Firm—Pennie & Edmonds LLP

(57) ABSTRACT

The present invention provides methods for preventing, treating, and/or managing one or more cancerous conditions in a patient, such as a human. A multivalent metal oxide, such as Ag(I,III), Cu(I,III), Pr(III,IV), and Bi(III,V) oxides or a pharmaceutically acceptable derivative thereof, may be administered to the patient in an amount and for a period of time which is therapeutically effective to prevent, treat, and/or manage such condition(s). These cancerous conditions include systemic and external cancers, and may also include conditions and symptoms associated with cancer. The present invention also provides a pharmaceutical composition suitable for treating such cancerous conditions. The compositions of the invention may be adapted for at least one of subcutaneous injection, intramuscular injection, intravenous injection, infusion, transdermal, or topical application.

31 Claims, No Drawings

METHODS OF USING ELECTRON ACTIVE COMPOUNDS FOR MANAGING CANCER

CROSS-REFERENCE TO RELATED APPLICATION

This application is a continuation-in-part of application Ser. No. 09/552,172, filed Apr. 18, 2000, now U.S. Pat. No. 6,258,385, and claims the benefit of Provisional Application No. 60/174,793, filed Jan. 6, 2000, No. 60/184,053, filed Feb. 22, 2000, and No. 60/214,503, filed Jun. 28, 2000.

FIELD OF THE INVENTION

The invention relates to pharmaceutical compositions including at least one metal oxide, such as an electron active metal oxide, and methods of using such compositions, for the prevention, treatment, and management of cancer and conditions or diseases related to the presence of cancer or a predisposition to cancer.

BACKGROUND OF THE INVENTION

Cancers are a leading cause of death in animals and humans. The exact cause of cancer is not known, but links between certain factors, such as smoking or exposure to carcinogens including tobacco smoke and chromium (VI), exposure to radiation, such as from x-rays, radioisotopes, and ultra-violet light, viruses, such as papaloma, Espstein Barr, and Raus sarcoma virus and the incidence of certain types of cancers and tumors has been shown by a number of researchers. Genetic factors and genome defects such as those found a chromosome 11 have also been linked to cancer. Traditional methods of cancer therapy include treatment with chemotherapeutic agents that inhibit cell division or radiation therapy that disrupts DNA in dividing cells. These treatments, however, may also adversely affect normal cells that happen to be dividing or synthesizing DNA at the time of treatment. Dosage levels low enough to insure survival of a cancer patient often are not sufficiently cytotoxic to tumor cells to retard continuing cell division after treatment. Additionally, the mechanism for the action of these chemotherapeutic agents is frequently unknown, which complicates the safe and effective use of these agents. Several different cancers and conditions associated with cancer are discussed below as examples illustrating the importance of combating cancer and associated conditions.

Breast carcinoma is the most common malignancy among women and shares with lung carcinoma the highest fatality rate of all cancers affecting females. For example, approximately one of every 11 women in the U.S.A. will develop breast cancer. For white women, the probability is about 1 in 10; for African American women, the rate is close to 1 in 14. The annual mortality rate from 1930 to the present has remained fairly constant at about 27 deaths per 1000,000 females, and is slightly higher for whites than African Americans.

In women, breast carcinoma is rare before age 30 but the incidence rises rapidly after menopause. Post-menopausal breast masses are typically considered cancerous until biopsy proves otherwise. Cystosarcoma phyllodes, which are a non-cancerous tumor, are the most common tumor of the breast; other malignancies are significantly more rare. Breast cancer in men is rare and tends not to be recognized until late with poor therapeutic results.

Most breast cancers, including those frequently designated as scirrhus, infiltrative, papillary, ductile, medullary, and lobular, appear as a slowly growing, painless mass, though a vague discomfort may be present. Physical signs typically include a retracted nipple, bleeding from the nipple, a distorted areola or breast contour, skin dimpling over the lesion, attachment of the mass to surrounding tissue, including the underlying fascia and overlying skin, edema of the skin of the breast with an orange peel appearance, and axillary or supraclavicular lymph nodes. In advanced cases, skin nodules with ultimate breakdown and ulcer formation may be seen.

The presence of metastases should always be suspected as the disease metastasizes by direct extension and via the lymph system and the bloodstream. Among the most common sites are the lungs and pleura, the skeleton (especially skull, spine, and pelvis), and the liver. Although the exact causes of breast cancer are not known, a doctor from France discovered a virus called mice breast tumor virus (vtmr) in 1985 that was later described as an oncomavirus with particules type B. This virus caused breast cancer in mice breast. It can be transmitted by breast milk or it can be incorporated in the human genome. Current treatments for breast cancer in general include surgery, radiotherapy, chemotherapy and hormonal therapy.

Cervical cancer includes those cancer moieties which are indigenous to the cervix. These cancer moieties are referred to generally as cervical carcinomas of which 85–90% are squamous cell carcinomas, and the balance are largely adenocarcinomas. The severity of cervical cancers are gauged by the clinical tests called PAP smears which indicate whether the carcinoma cells are confined to the cervix or have penetrated beyond it but not to the pelvic wall, or to the pelvic wall itself and even beyond the pelvis. Cervical cancers kill about 33% of their victims annually in the United States.

Carcinoma of the uterine cervix, the second most common malignancy of the female reproductive tract, most commonly affects women aged 40 to 56 years old. The incidence is higher among women from lower socioeconomic groups and among those with a history of early and frequent coitus and multiple sexual partners. Recently, venereal transmission of human papilloma virus (hpv) and herpes virus type 2 (nsv-2) have been implicated as important in the etiology of cervical neoplasia.

The earliest histologic change in what is considered a continuum from normal to invasive cancer is minimal cervical dysplasia, in which abnormal cell proliferation occurs in the lower third of the epithelium. Most of the minimal dysplasias are self-limiting and regress to normal tissue. Most severe dysplasias in the upper two-thirds of the epithelium showing abnormal proliferation, however, progress to carcinoma in situ, in which a full thickness of the epithelium contains abnormal calls. When cancer cells penetrate the basement membrane and invade the stroma (invasive carcinoma) they can spread by direct extension to adjacent pelvic organs or by lymphatic permeation and dissemination.

Of cervical carcinomas, 85 to 90% are squamous cell carcinoma. These vary from well-differentiated cells with keratinization to the highly anaplastic spindle cells of cervical tumors. Adenocarcinomas, observed in only 10 to 15% of cases, are more rare.

Early cervical neoplasia can be detected pre-clinically by cytologic examination of cervical smears obtained during routine annual pelvic examinations. At this stage, the disease is asymptomatic. The cervical smears (pap test) can detect 90% of early cervical neoplasias. Thus, the use of cervical smears has reduced the death rate from cervical cancer by more than 50% through recognition and treatment of pre-invasive neoplasia. Treatment of cervical cancer typically involves conization, radiotherapy, surgical therapy, and chemotherapy.

For diagnostic and prognostic purposes, the results of cervical smear tests may be grouped into four categories: class I characterized by the absence of observed abnormal cells; class II characterized by the presence of atypical cells and usually associated with inflammation; class III characterized by the presence of cells representative of or suspicious of carcinoma; and classes IV and V each characterized by the presence of carcinoma cells.

Additionally, the clinical stage or progression of the cervical carcinoma may be further characterized as follows. Stage 0 is characterized by carcinoma in situ with intra epithelial carcinoma. Stage I includes carcinomas strictly confined to the cervix. Stage IA is characterized by micro invasive carcinoma and stage IB is characterized by occult cancer.

In stage II, the carcinoma extends beyond the cervix but not onto the pelvic wall. Stage IIA exhibits no obvious parametrial involvement while stage IIB exhibits obvious parametrial involvement. In stage III, the carcinoma extends onto the pelvic wall. Stage IIIA is characterized by the lack of extension onto the pelvic wall and stage IIIB is characterized by extension onto the pelvic wall.

In stage IV, the carcinoma has extended beyond the true pelvis or has clinically involved the mucosa of the bladder. Stage IVA is characterized by the spread of the growth to adjacent organs. Stage IVB is characterized by the spread to distant organs.

Skin cancer is a disease in which cancer (malignant) cells are found in the layers of the skin. The skin has two main layers and several kinds of cells: a top layer called the epidermis, which contains three kinds of cells: flat, scaly cells on the surface called squamous cells; round cells called basal cells; and cells called melanocytes, which give the skin its color. The dermis is the inner, second layer of the skin.

The skin is the most environmentally-stressed organ in mammals, particularly in humans. The skin is subjected to toxic chemicals and hostile environments, as well as being the only organ directly exposed to ultraviolet ("UV") light in the presence of oxygen. Lengthy exposure of the skin to UV light typically damages the skin, resulting, in sunburn, photo-aging, carcinogenesis, and other related skin disorders. "Skin cancer" is generally used to describe the three major forms of skin cancer; basal cell and squamous carcinoma together with melanoma. These carcinomas account for about 97% of skin cancers. Melanoma, however, accounts for over 87% of deaths due to said cancers.

Melanoma is a disease of the skin in which cancer (malignant) cells are associated with the cells that color the skin (melanocytes). Melanoma usually occurs in adults, but it may occasionally be found in children and adolescents. Melanoma is sometimes called cutaneous melanoma or malignant melanoma. Melanoma can spread (metastasize) quickly to other parts of the body through the lymph system or through the blood.

About 80% of non-melanoma skin cancer will be basal cell carcinoma. It can occur at any location on the body surface, but occurs more commonly on sun-exposed surfaces, such as the face. The earliest sign may be a red flat area, a small nodule, a small spot that bleeds on rubbing, a small ulcer, or a scaly patch. About 20% of non-melanoma skin cancer will be squamous cell carcinoma. The difference between basal cell carcinoma and squamous cell carcinoma is often discernable only at the microscopic level, as the two may look identical. Squamous cell carcinoma, however, tends to grow more rapidly, and form an ulcer sooner. Squamous cell carcinoma may afflict any skin surface, but is common on the lips and ears.

Neurofibromatosis is a hereditary autosomal dominant disorder that is accompanied by a predisposition to cancer. Neurofibromatosis produces pigmented spots and tumors of the skin and of peripheral, optic and acoustic nerves. Subcutaneous and bony deformities may also be observed. One third of the patients with neurofibromatosis are asymptomatic and the condition is discovered during routine examination. In one-third of patients, cosmetic problems are the initial complaints. Characteristic skin lesions, apparent at birth or in infancy in 90% of the patients, include medium brown patches distributed most commonly over the trunk, pelvis, and flexor creases of elbows and knees. For diagnostic purposes, the presence of six or more of these freckle-like lesions with one larger than 1.5 cm is characteristic of neurofibromatosis. Multiple cutaneous tumors, flesh colored and of variable size and shape typically appear in late childhood.

The above-mentioned discussion merely illustrates the breadth and importance of cancer as an affliction of animals and humans in particular. Those of ordinary skill in the art will understand that various other types of cancers exist that also require suitable prevention, treatment, and/or management. In view of this discussion, there is a need for pharmaceutical compositions that can be administered at dosage levels low enough to insure survival of a cancer patient but which are sufficiently cytotoxic to cancer cells or cells associated with cancer to retard or eliminate continuing cell division after treatment, i.e., management or treatment of the cancer.

Metal oxides, such as electron active metal oxides comprising multivalent silver cations, have been disclosed for various uses, as they are reported to be non-toxic to animals and humans. M. Antelman, "Anti-Pathogenic Multivalent Silver Molecular Semiconductors," *Precious Metals*, vol. 16:141–149 (1992); M. Antelman, "Multivalent Silver Bactericides," *Precious Metals*, vol. 16:151–163 (1992). For example, tetrasilver tetroxide activated with an oxidizing agent is disclosed for use in bactericidal, fungicidal, and algicidal use, such as in municipal and industrial water treatment applications and for the treatment of AIDS.

A variety of sources also report the use of certain divalent silver compounds for water treatment, as well as the use of such compounds, typically in combination with certain oxidizing agents, metals, or other compounds, as disinfectants, bactericides, algicides, and fungicides. One source also reports a single in vitro study of the use of such compounds for the treatment of AIDS. These sources include M. Antelman, "Silver (II, III) Disinfectants," *Soap/Cosmetics/Chemical Specialties*, pp. 52–59 (March, 1994), and U.S. Pat. Nos. 5,017,295; 5,073,382; 5,078,902; 5,089,275; 5,098,582; 5,211,855; 5,223,149; 5,336,416; and 5,772,896.

U.S. Pat. No. 5,336,499 discloses tetrasilver tetroxide and persulfate compositions having certain in vitro anti-pathogenic properties, i.e., bactericidal, fungicidal, viricidal, and algicidal, in certain concentrations as low as 0.3 ppm, particularly in nutrient broth cultures. The persulfate is disclosed to be an oxidizing agent that activates the tetroxide crystals. Also disclosed are an in vitro study regarding the inhibition of yeast growth in nutrient broth and the formulation of a gynecological cream and douche based on these results, and a report of an in vitro AIDS test with the compositions indicating total suppression of the virus at 18 ppm.

In vitro assays, such as those disclosed in Ahmed, S. A., Gogal Jr., R. M. and Walsh, J. E., a New Rapid and Simple Non-radioactive Assay to Monitor and Determine the Proliferation of Lymphocytes: an Alternative to [$^3$H]-thymidine Incorporation Assay, Journal of Immunological Methods 1994; 170: 211–224; Boyd, M. R., Status of the NCI Preclinical Antitumor Drug Discovery Screen, J. B. Lippincott Company, Philadelphia, Principles & Practices of Oncology Updates 1989; 3 # 10: 1–12, and Boyd, M. R. et al. Data Display and Analysis Strategies for the NCI Disease-oriented in Vitro Antitummor Drug Screen in Cytotoxic Anti-cancer Drugs: Models and Concepts for Drug Discovery and Development, Kluwer Academic, Boston, 1992: 11–34; each of which is hereby incorporated herein in its entirety by express reference thereto, have been used to estimate the cyto-toxicity of anti-cancer therapeutics. One of ordinary skill in the art understands, however, that, although in vitro testing provides a useful screen for potentially useful compounds, animals such as humans are sufficiently complex that the actual in vivo cytotoxicity of a compound is often surprisingly different than that predicted upon the basis of an in vitro toxicity screen.

U.S. Pat. No. 5,571,520 discloses the use of molecular crystals of tetrasilver tetroxide, particularly with oxidizing agents to enhance the efficiency of such devices, for killing pathogenic microorganisms, such as staph infections. Amounts of 10 ppm sodium persulfate as an oxidizing agent were used with certain amounts of silver tetroxide in the reported in vitro testing. One human study involved in vivo curing of a gynecological yeast infection with 10 ppm of the silver tetroxide and 40 ppm sodium persulfate. Other in vivo topical studies report in conclusory fashion the cure of a single case of athlete's foot with a solution of 100 ppm of the composition and the cure of a single case of toenail fungus with a 25% suspension of the composition.

U.S. Pat. No. 5,676,977 discloses intravenously injected tetrasilver tetroxide crystals used for destroying the AIDS virus, AIDS synergistic pathogens, and immunity suppressing moieties (ISM) in humans. The crystals were formulated for a single injection at about 40 ppm of human blood. This reference also discloses the compositions cause hepatomegaly, also known as enlarged liver, albeit with no reported loss of liver function.

The aforementioned references report detailed descriptions of the mechanism via which the multivalent silver molecular crystal devices were believed to operate. The instant inventor also presented a discussion of such results and concepts at a Seminar entitled "Incurable Diseases Update" (Weizmann Institute of Science, Rehovot, Israel, Feb. 11, 1998). The title of this presentation was "Beyond Antibiotics, Non Toxic Disinfectants and Tetrasil™ (Trademark of applicant for the tetroxide)."

In this paper, it was reported that the effects of the electron transfer involved with respect to the tetroxide, rendered it a more powerful germicide than other silver entities. The instant inventor holds patents for multivalent silver antimicrobials, e.g., U.S. Pat. No. 5,017,295 for Ag(II) and U.S. Pat. No. 5,223,149 for Ag (III); and while these entities are stronger antimicrobials than Ag (I) compounds, they pale by comparison to the tetroxide and so does colloidal silver that derives its germicidal properties from trace silver (I) ions it generates in various environments. Accordingly, the oligodynamic properties of these entities may be summarized as follows, which is referred to as the Horsfal series:

$$Ag_4O_4 > Ag(III) > Ag(II) >>>> Ag(I)$$

The other unique property of the tetroxide was that it did not stain organic matter such as skin in like manner as Ag(I) compounds do. In addition, it was light stable.

Thus, it is desired to find pharmaceutical compositions and methods for preventing, treating, or managing one or more cancers or associated conditions. It is also desired to facilitate the prevention of future outbreaks of one or more disorders, as well as preventing, treating, and managing one or more cancerous or related disorder while avoiding the adverse effects present in many conventional treatments.

SUMMARY OF THE INVENTION

The present invention relates to a method for preventing, treating, or managing one or more cancerous conditions or dysplastic proliferations in an animal. The method preferably comprises administering at least one metal oxide compound or a pharmaceutically acceptable derivative thereof, to the animal. The metal oxide compound or derivative thereof preferably comprises a first metal cation having a first valence state and a second metal cation having a second, different valence state, such as, for example, an electron active metal oxide compound. The at least one metal oxide compound or a pharmaceutically acceptable derivative thereof is preferably administered in an amount and for a period of time which is therapeutically effective to treat such condition(s).

In a preferred embodiment, the at least one metal oxide compound or pharmaceutically acceptable derivative thereof comprises at least one of Bi(III,V) oxide, Co(II,I) oxide, Cu(I,III) oxide, Fe(II,III) oxide, Mn(II,III) oxide, Pr(III,IV) oxide, or Ag(I,III) oxide.

The metal oxide compound or derivative thereof is preferably substantially free of added persulfate.

The invention is preferably adapted to preventing, treating, or managing systemic cancerous conditions. Preferably, the animal is an mammal, such as, for example, a human. The metal oxide compound is preferably administered via intravenous injection or infusion, when the animal is a human. The intravenous injection or infusion is preferably subcutaneous, intramuscular, or comprises infusion into the bloodstream of the animal. Preferably, the administration provides an amount of the metal oxide sufficient to provide about 1 to about 75 ppm of the metal oxide compound or derivative thereof in the bloodstream. The metal oxide is preferably administered via infusion over a period of time sufficient to inhibit adverse side effects, such as over a time period of from about 30 minutes to about 300 minutes.

The metal oxide compound or derivative thereof may preferably be administered by a controlled release vehicle. The controlled release vehicle is preferably implanted in the body at a location suitable for providing a therapeutically effective amount of metal oxide compound or derivative thereof to the patient, preferably, without affecting proper functioning of the animal's liver.

The method of the invention is preferably suitable for cancers or dysplastic proliferations including at least one of colon cancer, lung cancer, throat cancer, breast cancer, kidney cancer, pancreatic cancer, bladder cancer, prostate cancer, uterine cancer, brain cancer, liver cancer, skin cancer, testicular cancer, stomach cancer, adrenal gland cancer, cancer of the ovaries, thyroid cancer, bronchial cancer, tracheal cancer, eye cancer, bone cancer, cervical cancer, oral cavity cancer, soft tissue cancer, pituitary gland cancer, myeloma, rectal cancer, esophageal cancer, leukemia, lymphoma, cancerous fibroid tumors, non-cancerous fibroid tumors, or liver cancer. The method is preferably suitable for cancers including skin cancer that has metastasized.

In a preferred embodiment, the metal oxide compound or derivative thereof is administered in conjunction with at least one other chemotherapeutic agent. The at least one other chemotherapeutic agent is preferably administered concurrently with the metal oxide compound or derivative thereof.

Another embodiment of the invention relates to a method for preventing, treating, or managing one or more cancerous conditions or dysplastic proliferations associated with a patient's skin, which method preferably comprises administering at least one metal oxide compound or a pharmaceutically acceptable derivative thereof to the skin in an amount and for a period of time which is therapeutically effective to treat such cancerous or associated condition(s). The metal oxide compound or derivative thereof preferably comprises a first metal cation having a first valence state and a second metal cation having a second, different valence state.

In a preferred embodiment, the at least one metal oxide compound or pharmaceutically acceptable derivative thereof comprises at least one of Bi(III,V) oxide, Co(II,III) oxide, Cu(I,III) oxide, Fe(II,III) oxide, Mn(II,III) oxide, Pr(III,IV) oxide, or Ag(I,III) oxide.

The metal oxide compound or derivative thereof is preferably substantially free of added persulfate.

The method of the invention is preferably suitable for preventing, treating, or managing cancerous conditions or dysplastic proliferations comprising at least one of dysplastic nevi, neurofibromatosis, basal cell carcinoma, squamous carcinoma, or melanoma. The method is preferably suitable for preventing, treating, or managing conditions comprising symptoms of cancer or conditions associated with a predisposition to cancer, such as neurofibromatosis.

The administering preferably comprises a carrier medium in which the at least one metal oxide compound or pharmaceutically acceptable derivative thereof, is dispersed. Preferably the therapeutically effective amount of the metal oxide or derivative thereof is from about 50 ppm to 500,000 ppm, such as from about 400 ppm to about 100,000 ppm, based on the weight of the carrier medium. The carrier medium may preferably comprise petroleum jelly. The administering of the composition is preferably topical or transdermal, such as directly to the skin.

Preferably, the at least one metal oxide compound or pharmaceutically acceptable derivative thereof, further comprises a thixotropic agent sufficient to increase adherence of the composition to the skin without excessive runoff.

The at least one metal oxide compound or pharmaceutically acceptable derivative thereof may, preferably, be administered in the form of a powder, such as in the form of metal oxide crystals. The administering of the powder is preferably topical or transdermal, such as directly to the skin. Preferably the metal oxide or derivative thereof is administered at a dosage level of about 10 mg to 500 mg per $cm^2$ of skin surface. A preferred embodiment of a composition suitable for application as a powder comprises about 5% metal oxide, such as tetrasilver tetroxide, and about 95% bismuth subgallate.

Yet another embodiment of the invention relates to a method for preventing, treating, or managing one or more cancerous conditions associated with a cervix of a female animal. The method preferably comprises administering at least one metal oxide compound or a pharmaceutically acceptable derivative thereof to the cervix in an amount and for a period of time which is therapeutically effective to treat such cancerous or associated condition(s). Each metal oxide compound or derivative thereof preferably comprises a first metal cation having a first valence state and a second metal cation having a second, different valence state.

In a preferred embodiment, the at least one metal oxide compound or pharmaceutically acceptable derivative thereof comprises at least one of Bi(III,V) oxide, Co(II,III) oxide, Cu(I,III) oxide, Fe(II,III) oxide, Mn(II,III) oxide, Pr(III,IV) oxide, or Ag(I,III) oxide.

The metal oxide compound or derivative thereof is preferably substantially free of added persulfate.

The metal oxide compound or derivative thereof are preferably applied directly to the cervix. The administering preferably comprises a carrier medium, such as petroleum jelly, in which the at least one metal oxide compound or pharmaceutically acceptable derivative thereof, is dispersed, preferably in a therapeutically effective amount from about 50 ppm to 500,000 ppm, based on the weight of the carrier medium. The at least one metal oxide compound or pharmaceutically acceptable derivative thereof is preferably applied in an amount sufficient to obtain a desired effect and to substantially inhibit undesirable side effects.

Definitions Section

Suitable definitions are provided herein for some of the terms relating to the present invention.

The terms "patient" or "subject" as used herein refer to animals, particularly to mammals. In a preferred embodiment, the terms "patient" or "subject" refer to humans.

As used herein, the terms "adverse effects," "adverse side effects," and "side effects" include, but are not limited to, staining of the skin, headache, dry mouth, constipation, diarrhea, gastrointestinal disorders, dry skin, staining of the skin, hepatomegaly, fever, fatigue, and the like.

The phrase "therapeutically effective amount" when used herein in connection with the compositions and methods of the invention, means that amount of metal oxide composition, or a derivative thereof, which, alone or in combination with other drugs or treatment modalities, provides a therapeutic benefit in the prevention, treatment, or management, of one or more of forms of cancer or a symptom or related condition thereof. Preferably, the therapeutically effective amount of a component yields the desired therapeutic benefit without undue adverse side effects (such as toxicity, irritation, or allergic response) commensurate with a reasonable benefit/risk ratio when used in the manner of this invention.

The term "substantially free" means less than about 10 weight percent, preferably less than about 5 weight percent, more preferably less than about 1 weight percent, and most preferably less than about 0.1 weight percent of added persulfate is present according to the invention. In another embodiment, the term "substantially free" refers to the same amounts of other added oxidizing agents present in the compositions.

The term "controlled-release component" in the context of the present invention is defined herein as a compound or compounds, including polymers, polymer matrices, gels, permeable membranes, liposomes, microspheres, or the like, or a combination thereof, that facilitates the controlled-release of the active ingredient (e.g., tetrasilver tetroxide) in the pharmaceutical composition.

The term "about," as used herein, should generally be understood to refer to both numbers in a range of numerals.

DETAILED DESCRIPTION OF THE PREFERRED EMBODIMENTS

Moreover, all numerical ranges herein should be understood to include each whole integer within the range.

It has now been discovered that pharmaceutical compositions comprising at least one oxide compound or a pharmaceutically acceptable derivative thereof can be used as advantageous active ingredients in the prevention, treatment, or management of various cancerous conditions. The oxide compound preferably comprises a metal oxide, such as an electron active metal oxide. The metal oxide compound or pharmaceutically acceptable derivative thereof preferably comprise a first metal cation having a first valence state and a second metal cation having a second, different valence state. One of ordinary skill in the art understands that, in general, the valence state of a species, such as a metal cation, is related to the charge associated with or assigned to the species.

Preferably, the at least one metal oxide compound or a pharmaceutically acceptable derivative comprises at least one electron active metal oxide compound, such as, for example, at least one of Bi(III,V) oxide, Co(II,III) oxide, Cu(I,III) oxide, Fe(II,III) oxide, Mn(II,III) oxide, Pr(II,IV) oxide, or Ag(I,III) oxide. Preferred compounds of the invention comprise at least one metal tetroxide, such as silver tetroxide. The terms metal tetroxide and metal tetraoxide, are synonymous as used herein.

In one preferred embodiment, the metal oxide compound compositions are substantially free of added persulfate or other added oxidizing agents, since, when applied topically, such agents may cause adverse effects, such as skin irritation and skin over-drying. In another preferred embodiment, the compositions are substantially free of any oxidizing agents. More particularly, the invention relates to methods for preventing, treating, and managing cancerous conditions and conditions associated with cancer.

In one embodiment, the compositions include a molecular scale device comprising at least one crystal of a metal oxide compound. A plurality of these metal oxide crystals, such as on the order of trillions, may be employed in various pharmaceutical formulations and therapies to effectuate the prevention, treatment, and/or management of various cancers and conditions associated with cancer. The compositions of the invention include powders comprising metal oxide crystals of the invention.

The compositions and methods of the invention advantageously provide a desired effect such as preventing, treating, or managing cancer or conditions associated with cancer. "Management," as used herein, includes controlling one or more cancers, or conditions associated with such cancer(s), that cannot be cured completely, reducing the severity of affliction of such cancers or related conditions, and the like. Thus, a preferred embodiment of the invention relates to a method of inducing cytotoxicity (cell killing) in cancer cells or reducing the viability of cancer cells. In one embodiment, the invention relates to the treatment or management of cancer and/or diseases or conditions associated with cancer, while in another embodiment the invention relates to the prevention, of cancer and/or diseases or conditions associated with cancer.

Preferred metal oxides of the invention comprise a first metal cation having a first valency state and a second metal cation having a second valency state, which differs from the first valency, preferably by at least one charge. The first and second metal cations are preferably the same metal. Without being bound by theory, it is believed that the metal oxides of the present invention operate by transferring electrons between cations of differing valency, the electrons contributing to the death of the cancer cells by traversing the cell membrane. By way of non-limiting example, it is believed that the crystal lattice of a silver tetroxide ($Ag_4O_4$) molecular device operates against cancer, tumors, or cells associated with cancer by transferring electrons from its two monovalent silver ions to the two trivalent silver ions in the crystal, contributing to the death of the cancer cells by traversing their cell membrane surface. This in effect "electrocutes" the cancer cells. The electrons are forced out of their balanced crystals by such labile groups as NH, $NH_2$, S—S, and SH associated with the cellular surface. Normal cells are not believed to be affected, because they are not believed to proliferate fast enough to expose these labile bonds.

The metal oxides of the invention are preferably stable as determined by the dissociation constants of the compounds. For example, the dissociation constant ($K_A$) of $Ag_4O_4$ is $7.9 \times 10^{-13}$. Therefore the molecule is not believed to be disturbed unless more stable complexes are formed with such ligands as those associated with the cancer cell membrane surface in a dynamic state. Indeed, the end result of the electron transfer, which is a redox reaction, is believed to result in the metal ions of a lower valency being oxidized to a higher valency state and metal ions of a higher valency state being reduced to a lower valency state.

Returning to the non-limiting example of silver tetroxide, it is believed that monovalent Ag ions are oxidized to Ag(II) and the trivalent Ag ions are reduced to the same end product, Ag(II). Accordingly, the well-known affinity of monovalent silver for certain elements such as sulfur and nitrogen is believed to be far exceeded here, for divalent silver is believed to not merely bind to these elements as does silver, but to actually form chelate complexes with their ligands. The molecular crystal attraction for the cell membrane surfaces is thus believed to be driven by powerful covalent bonding forces.

The electron transfer occurring in the example of silver tetroxide can be depicted by the following redox half reactions:

$$Ag^+ - e = Ag^{+2}$$

$$Ag^{+3} + e = Ag^{+2}$$

It was found by rigorous testing that certain silver tetroxide containing-compositions were comparatively non- toxic in comparison to monovalent silver salts. Since these silver tetroxide compositions were effective at certain ppm concentrations in killing pathogens in nutrient broth and for water treatment, commercial concentrates were formulated with 2% of the tetroxide. Prior to the acceptance of the oxide in commerce, for which EPA registration No. 3432-64 was obtained, it was necessary for the oxide to undergo a series of toxicity tests. A 3% concentrate was used and evaluated by a certified laboratory employing good laboratory practice (GLP) according to the Code of Federal Regulations for this purpose.

The results were as follows:

| | |
|---|---|
| Acute Oral Toxicity | $LD_{50}$ Greater than 5,000 mg/Kg |
| Acute Dermal Toxicity | $LD_{50}$ Greater than 2,000 mg/Kg |

-continued

| | |
|---|---|
| Primary Eye Irritation | Mildly irritating |
| Primary Skin Irritation | No irritation |
| Skin Sensitization | Non-Sensitizing |

Subsequent evaluations conducted according to the invention showed that unless persons were prone to silver allergies, the pure tetroxide compositions according to the invention could be applied to, for example, the skin without any ill effects or evidence of irritation, despite the fact that the compositions of the invention can be a powerful oxidizing agent. This can perhaps be explained by the stability manifested by the above-noted $K_A$ of the silver compositions. Accordingly, in a preferred embodiment, the metal oxides of the invention are applied directly in a powder or composition form to afflicted areas, such as the skin, cervix, or cervical pelvic region of an animal afflicted with cancer. Preferred routes of administration include topically and application to mucosa. Application can be made, for example, digitally or using a suitable applicator.

One embodiment of the present invention relates to compositions and methods of using the metal oxide compositions of the invention while minimizing the amount of additional oxidizer, such as persulfate. It has been found in accordance with the present invention that the additional oxide is not required and in some circumstances is undesirable when the oxide is applied to, for example, the skin or cervix, in part due to the undesirable side effect of irritation. In one embodiment, the compositions are substantially free of added persulfates, while in a preferred embodiment, the compositions are completely free of added persulfates. In one preferred embodiment, the compositions are substantially free of added oxidizer, while in another preferred embodiment they are completely free of added oxidizer. The aforementioned compositions may be applied topically or to mucosa associated with, for example, the skin, cervix, vagina, or colon.

The metal oxide compound, such as tetrasilver tetroxide, may be black in color, such that care must be taken when formulating suitable topical pharmaceutical compositions according to the invention to inhibit or avoid blackening or staining of the skin. Without being bound by theory, it is believed that larger amounts of the silver tetroxide composition promote increased staining. Thus, in one embodiment, the pharmaceutical compositions preferably have an insufficient amount of metal oxide compound to cause visible skin staining.

Where the metal oxide compositions according to the invention are applied to the skin, they may be combined with a carrier at an amount from about 5 ppm to 500,000 ppm, more preferably from about 50 ppm to 250,000 ppm of the metal oxide composition, based on the weight of the carrier. In various embodiments, the compositions are provided in amounts from about 400 ppm to 100,000 ppm, from about 1,000 ppm to 70,000 ppm, from about 10,000 ppm to 50,000 ppm, or from about 20,000 ppm to 40,000 ppm. In one preferred embodiment, the compositions are formulated with about 25,000 ppm to 35,000 ppm of metal oxide. It will be readily understood by those of ordinary skill in the art that the administration of 0.005 g of metal oxide to an adult human being provides about 1 ppm of the metal oxide in the bloodstream of the human. In another embodiment, the concentration of the metal oxide crystals dispersed in the carrier ranges from about 0.1 to 10% by weight, more preferably from about 0.25 to 5% by weight and most preferably from about 2 to 4% by weight. The compositions, when applied topically, can be applied to the skin about 1 to 3 times per day until the condition is suitably cured or satisfactorily controlled. In one embodiment, the composition may generally be topically applied at a dosage level of from about 1 mg to 1000 mg per $cm^2$ of skin surface, preferably about 10 mg to 500 mg per $cm^2$ of skin surface.

A preferred carrier for topical formulations and administration includes petroleum jelly, such as white petroleum jelly. For example, a suitable white petroleum jelly is available from Penreco of Houston, Tex.

A preferred mode of application of the oxide of the invention is as an ointment. Suitable formulations include, but are not limited to, salves and the like. If desired, these may be sterilized or mixed with auxiliary agents, e.g., thixotropes, stabilizers, wetting agents, and the like. Preferred vehicles include ointment bases, e.g., polyethylene glycol-1000 (PEG-1000); conventional ophthalmic vehicles; creams; and gels, as well as petroleum jelly and the like.

The cancerous conditions and diseases that may be prevented, treated, or managed with the compositions of the invention vary and include, but are not limited to, cancers including any of the various malignant neoplasms, tumors, or cells, such as, for example, those marked by a proliferation of anaplastic cells. In particular, the term cancer includes any cancers that involve specific organs or regions of the body such as the colon, lung, throat, breast, kidney, pancreas, bladder, prostate, uterus, brain, liver, skin, testicles, stomach, adrenal gland, ovaries, thyroid, rectum, bronchus, trachea, eye, bone, cervix, oral cavity, soft tissue, pituitary gland, myeloma, rectum, esophagus or liver. The invention is also suited for the prevention, treatment, or management of cancerous fibroid tumors and non-cancerous fibroid tumors. Prevention, treatment, or management of any of the above conditions, as well as any others described herein, individually or in any combination, simultaneously or concurrently, is contemplated according to the invention.

Also included are various cell proliferations such as leukemia, which is a malignant overproduction of white blood cells, lymphoma, and metastasized melanoma which has proliferated from skin via blood and/or the lymphatic system. Conditions or diseases associated with a predisposition to cancer, such as, for example, neurofibromatosis are also included. The present invention preferably allows treatment or management of conditions or diseases associated with a predisposition to cancer even if those conditions or diseases have not fully progressed to a cancerous or malignant stage.

The present invention is also adapted to treating or managing atypical proliferations of cells, such as those characterized by nuclear enlargement and failure of maturation and differentiation. Such proliferations may be short of malignancy. Atypical proliferations suitable for treatment, management, or prevention by the present invention include dysplasia or dysplastic proliferations, such as dysplastic nevi or neurofibromatosis, which are recognized by alterations in the appearance of cells (cytology). Dysplastic cells may have some of the features of malignant cells but the changes are less pronounced. As the dysplasia progresses, the nuclei of cells become more hyperchromatic and the nuclear membranes become more irregular; the size of the nucleus increases and the cytoplasm does not increase proportionately, so the that the nuclear:cytoplasmic ratio increases.

Different therapeutically effective amounts and deliver systems may be applicable for each disorder, as will be readily known or determined by those of ordinary skill in the art.

Tumors or neoplasms include new growths of tissue in which the multiplication of cells is uncontrolled and progressive. Some such growths are benign, but others are termed "malignant," leading to death of the organism. Malignant neoplasms or "cancers" are distinguished from benign growths in that, in addition to exhibiting aggressive cellular proliferation, they invade surrounding tissues and metastasize. Moreover, malignant neoplasms are characterized in that they show a greater loss of differentiation (greater "dedifferentiation"), and a greater loss of their organization relative to one another and their surrounding tissues. This property is also called "anaplasia."

Neoplasms preventable, treatable, or manageable by the present invention include all solid tumors, i.e., carcinomas and sarcomas. Carcinomas include those malignant neoplasms derived from epithelial cells which tend to infiltrate (invade) the surrounding tissues and give rise to metastases. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue.

The invention can also be practiced by administering the metal oxide compositions in conjunction with one or more other anti-cancer compatible chemotherapeutic agents, such as any conventional chemotherapeutic agent. The combination of the metal oxide with such other agents can potentiate the chemotherapeutic protocol. Numerous chemotherapeutic protocols will present themselves in the mind of the ordinary-skilled practitioner as being capable of use according to the methods of the invention. Any compatible chemotherapeutic agent can be used, including antimetabolites, hormones and antagonists, radioisotopes, as well as natural products. For example, the metal oxide can be administered with taxol and its natural and synthetic derivatives, and the like, and combinations thereof. As another example, in the case of mixed tumors, such as adenocarcinomas of the breast and prostate, in which the tumors can include gonadotropin-dependent and gonadotropin-independent cells, the metal oxide can be administered in conjunction with leuprolide or goserelin (synthetic peptide analogs of LH-RH), or both. Other antineoplastic protocols include the use of a metal oxide with another treatment modality, e.g., surgery, radiation, other chemotherapeutic agent, etc., referred to herein as "adjunct antineoplastic modalities." Thus, the method of the invention can be employed with such conventional regimens with the benefit of reducing side effects and enhancing efficacy. These other anti-cancer chemotherapeutic agents and modalities may be administered either concurrently or sequentially with the metal oxide compositions of the invention.

A preferred metal oxide for use according to the invention, tetrasilver tetroxide, has been commercially sold under the poorly named "Ag(II) OXIDE" tradename. It may also be obtained from Aldrich Chemical Co., Milwaukee, Wis. The chemical synthesis of silver oxide compounds according to the invention can be performed according to the method described on page 148 in M. Antelman, "Anti-Pathogenic Multivalent Silver Molecular Semiconductors," *Precious Metals,* vol. 16:141–149 (1992) by reacting silver nitrate with potassium peroxydisulfate according to the following equation in alkali solutions:

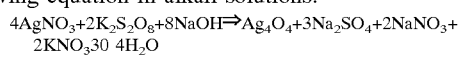
$4AgNO_3 + 2K_2S_2O_8 + 8NaOH \Rightarrow Ag_4O_4 + 3Na_2SO_4 + 2NaNO_3 + 2KNO_3 30 4H_2O$ The magnitude of a prophylactic or therapeutic dose of metal oxide composition(s), or a derivative thereof, in the acute or chronic management of diseases and disorders described herein will vary with the severity of the condition to be prevented, treated, or managed and the route of administration. For example, oral, mucosal (including vaginal and rectal), parenteral (including subcutaneous, intramuscular, bolus injection, and intravenous, such as by infusion), sublingual, transdermal, nasal, buccal, and like may be employed. Dosage forms include tablets, troches, lozenges, dispersions, suspensions, suppositories, solutions, capsules, soft elastic gelatin capsules, patches, and the like. The dose, and perhaps the dose frequency, will also vary according to the age, body weight, and response of the individual patient. Suitable dosing regimens can be readily selected by those of ordinary skill in the art with due consideration of such factors.

In general, for topical and mucosal application, such as application to the skin or cervix, the total daily dosage for the conditions described herein can be from about 1 mg to 500 mg of the metal oxide or derivative thereof, while in another embodiment, the daily dosage can be from about 2 mg to 200 mg of the metal oxide composition. A unit dosage can include, for example, 30 mg, 60 mg, 90 mg, 120 mg, or 200 mg of metal oxide composition. Preferably, the active ingredient is administered in single or divided doses from one to four times a day.

In another embodiment, the compositions are administered by an oral route of administration. The oral dosage forms may be conveniently presented in unit dosage forms and prepared by any methods available to those of ordinary skill in the art of pharmacy.

In managing the patient, the therapy may be initiated at a lower dose, e.g., from about 1 mg, and increased up to the recommended daily dose or higher depending on the patient's global response. It is further recommended that children, patients over 65 years, and those with impaired renal or hepatic function, initially receive low doses when administered systemically, and that they be titrated based on individual response(s) and blood level(s). It may be necessary to use dosages outside these ranges in some cases, as will be apparent to those of ordinary skill in the art. Furthermore, it is noted that the clinician or treating physician will know how and when to interrupt, adjust, or terminate therapy in conjunction with individual patient response.

Any suitable route of administration may be employed for providing the patient with an effective dosage of metal oxide, or a pharmaceutically acceptable derivative thereof. The most suitable route in any given case will depend on the nature and severity of the condition being prevented, treated, or managed. One preferred route is parenterally, preferably intravenously. In this embodiment, a preferred intravenous route of administration is by infusion.

In practical use, metal oxide, or a derivative thereof, can be combined as the active ingredient in intimate admixture with a pharmaceutical carrier according to conventional pharmaceutical compounding techniques. The carrier may take a wide variety of forms and may include a number of components depending on the form of preparation desired for administration. The compositions of the present invention include, but are not limited to, suspensions, solutions and elixirs; aerosols; or carriers, including, but not limited to, starches, sugars, microcrystalline cellulose, diluents, granulating agents, lubricants, binders, disintegrating agents, and the like.

Another suitable route of administration of the silver tetroxide compositions of the invention is topically, e.g., either directly as a powder or in non-sprayable or sprayable form. Topical administration is a preferred route of administration for treating topical cancerous conditions, such as skin cancer that has not metastasized or cervical cancer. In one embodiment, the metal oxide may be applied topically to the affected skin areas directly in powder form or in compounded formulations.

Non-sprayable forms can be semi-solid or solid forms including a carrier indigenous to topical application and preferably having a dynamic viscosity greater than that of water. Suitable formulations include, but are not limited to, suspensions, emulsions, creams, ointments, powders, liniments, salves and the like. If desired, these may be sterilized or mixed with any available auxiliary agents, carriers, or excipients, e.g., thixotropes, stabilizers, wetting agents, and the like. One or more thixotropic agents can be included in types and amounts sufficient to increase adhesion of topically applied compositions of the invention to a surface or mucosa associated with a treatment zone such as, for example, the skin, vagina, or cervix, so as to inhibit or prevent runoff or other loss of the composition from the treatment zone, particularly when the compositions are formulated for topical administration. With respect to conditions associated with the skin, the compositions preferably prevent, treat, or manage such conditions or diseases without visibly staining the skin, i.e., no staining to the naked eye.

Preferred vehicles for non-sprayable topical preparations include ointment bases, e.g., polyethylene glycol-1000 (PEG-1000); conventional ophthalmic vehicles; creams; and gels, as well as petroleum jelly and the like. In one preferred topical embodiment, the carrier includes a petroleum jelly. In another preferred topical embodiment, the carrier is formulated as a cream, gel, or lotion. A preferred composition comprises about 3% metal oxide, such as tetrasilver tetroxide, about 47% white petrolatum, about 36% heavy mineral oil, and about 14% TIVAWAX P Tivian Laboratories Inc., Providence, R.I. These topical preparations may also contain emollients, perfumes and/or pigments to enhance their acceptability for various uses.

In a preferred embodiment, a metal oxide, or a derivative thereof, is formulated for parenteral administration by injection (subcutaneous, bolus injection, intramuscular, or intravenous, such as by infusion), and may be dispensed in a unit dosage form, such as a multidose container or an ampule. Parenteral administration is a preferred administration route when the cancer is systemic, i.e., has a locus inside the body. Preferably, the formulation adapted for parenteral administration includes an insufficient amount of persulfate to induce irritation or adverse side effects. In one preferred embodiment, the formulation is substantially free of added persulfate, while in another more preferred embodiment, the formulation is completely free of added persulfate.

When administered intravenously, such as by infusion, the dosage preferably provides a concentration of the metal oxide in the blood stream of about 1 ppm to about 75 ppm, more preferably from about 5 ppm to about 50 ppm, such as from about 10 ppm to about 40 ppm or about 50 to 200 mg. In a preferred embodiment, a one-time dosage is infused or injected directly into the bloodstream.

The intravenous dosage is preferably delivered over a period of time sufficient to substantially inhibit or even avoid the occurrence of side effects. For example, the dosage can be delivered by intravenously or by infusion over a time from about 10 minutes to about 300 minutes, preferably from about 20 minutes to about 240 minutes.

Compositions of the metal oxide, or a pharmaceutically acceptable derivative thereof, for parenteral administration may be in the form of suspensions, solutions, emulsions, or the like, in aqueous or oily vehicles, and in addition to the active ingredient may contain one or more formulary agents, such as dispersing agents, suspending agents, stabilizing agents, preservatives, and the like.

Pharmaceutical compositions of the present invention may be orally administered in discrete pharmaceutical unit dosage forms, such as capsules, cachets, soft elastic gelatin capsules, tablets, or aerosols sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the pharmaceutically acceptable carrier which constitutes one or more necessary ingredients. In general, the compositions are prepared by uniformly and intimately admixing the active ingredient with liquid carriers or finely divided solid carriers or both, and then, if necessary, shaping the product into the desired presentation. Suitable types of oral administration include oral solid preparations, such as capsules or tablets, or oral liquid preparations. If desired, tablets may be coated by standard aqueous or non-aqueous techniques.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, granulating agent, surface active agent, dispersing agent, or the like. Molded tablets may be made by molding, in a suitable machine, a mixture of the powdered compound moistened with an inert liquid diluent. In one embodiment, each tablet, capsule, cachet, or gel cap contains from about 0.5 mg to about 500 mg of the active ingredient, while in another embodiment, each tablet contains from about 1 mg to about 250 mg of the active ingredient. The amount of active ingredient found in the composition, however, may vary depending on the amount of active ingredient to be administered to the patient.

Another suitable route of administration is transdermal delivery, for example, via an abdominal skin patch.

The metal oxide, or a suitable derivative thereof, may be formulated as a pharmaceutical composition in a soft elastic gelatin capsule unit dosage form by using conventional methods well known in the art, such as in Ebert, *Pharm. Tech,* 1(5):44–50 (1977). Soft elastic gelatin capsules have a soft, globular gelatin shell somewhat thicker than that of hard gelatin capsules, wherein a gelatin is plasticized by the addition of plasticizing agent, e.g., glycerin, sorbitol, or a similar polyol. The hardness of the capsule shell may be changed by varying the type of gelatin used and the amounts of plasticizer and water. The soft gelatin shells may contain a preservative, such as methyl- and propylparabens and sorbic acid, to prevent the growth of fungi. The active ingredient may be dissolved or suspended in a liquid vehicle or carrier, such as vegetable or mineral oils, triglycerides, surfactants such as polysorbates, or a combination thereof.

In the case of tumors having loci inside the body, e.g., brain tumors, prostate tumors, and the like, the metal oxide can be delivered via a controlled release delivery vehicle. In a preferred embodiment, the controlled release vehicle includes a polymeric material, delivered or surgically implanted at or near the lesion site. One of ordinary skill in the art will be familiar with controlled release means and delivery devices, such as those described in U.S. Pat. Nos.: 3,845,770; 3,916,899; 3,536,809; 3,598,123; 4,008,719; 5,674,533; 5,059,595; 5,591,767; 5,120,548; 5,073,543;

5,639,476; 5,354,556; and 5,733,566, the disclosures of which are hereby incorporated herein by express reference thereto. These pharmaceutical compositions can be used to provide slow or controlled-release of the active ingredient therein using, for example, hydropropylmethyl cellulose in varying proportions to provide the desired release profile, other polymer matrices, gels, permeable membranes, osmotic systems, multilayer coatings, microparticles, liposomes, microspheres, or the like, or a combination thereof. Suitable controlled-release formulations available to those of ordinary skill in the art, including those described herein, may be readily selected for use with the metal oxide compositions of the invention. Thus, single unit dosage forms suitable for topical, parenteral, or oral administration, such as infusions, intravenous drips, gels, lotions, cremes, tablets, capsules, gelcaps, caplets, and the like, that are adapted for controlled-release are encompassed by the present invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include: 1) extended activity of the drug; 2) reduced dosage frequency; and 3) increased patient compliance.

Most controlled-release formulations are designed to initially release an amount of drug that promptly produces the desired therapeutic effect, and gradual and continual release of other amounts of drug to maintain this level of therapeutic effect over an extended period of time. In order to maintain this constant level of drug in the body, the drug should be released from the dosage form at a rate that will replace the amount of drug being metabolized and excreted from the body.

The controlled-release of the active ingredient may be stimulated by various inducers, for example pH, temperature, enzymes, water, or other physiological conditions or compounds. The pharmaceutical compositions for use in the present invention include the metal oxide, or a derivative thereof, as the active ingredient, and may also contain a pharmaceutically acceptable carrier, and optionally, other therapeutic ingredients. Suitable derivatives include any available "pharmaceutically acceptable salts," which refer to a salt prepared from pharmaceutically acceptable non-toxic acids including inorganic acids, organic acids, solvates, hydrates, or clathrates thereof. Preferably, in the case of silver (I,III), the salts do not comprise halides. Examples of such inorganic acids are hydrochloric, hydrobromic, hydroiodic, nitric, sulfuric, and phosphoric. Appropriate organic acids may be selected, for example, from aliphatic, aromatic, carboxylic and sulfonic classes of organic acids, examples of which are formic, acetic, propionic, succinic, citric, fumaric, gluconic, isethionic, lactic, malic, mucic, tartaric, para-toluenesulfonic, glycolic, glucuronic, maleic, furoic, glutamic, salicylic, mandelic, methanesulfonic, ethanesulfonic, benzenesulfonic (besylate), sulfanilic, alginic, galacturonic, and the like. Particularly preferred acids phosphoric, methanesulfonic, and glycolic.

EXAMPLES

These and other aspects of the present invention may be more fully understood with reference to the following non-limiting examples, which are merely illustrative of the preferred embodiment of the present invention, and are not to be construed as limiting the invention, the scope of which is defined by the appended claims.

Example 1

Treatment of Breast Cancer According to the Invention

A subject group was formed of thirty female residents of Central America aged 32 to 52 years who had been diagnosed as having breast cancer. The subjects had the following general characteristics: 38% were older than 45 years old; 47% had never borne children; 60% were around menopause;18% had their first period before age 13 years; 60% of had used oral contraceptives; 38% of the subjects had cancers associated with the left breast; and 40% of the subjects had a family history of breast cancer. The diagnosis of each subject was confirmed by biopsy and a mammogram was acquired from each subject.

Each subject was evaluated daily by an oncologist(s) and each received a single dosage of tetrasilver tetroxide by IV, i.e., intravenously, sufficient to provide a concentration in the bloodstream of 10 ppm. One-half of the patients received the dosage in 10 minutes by IV injection. The other half of the subjects received the dosage by IV injection over a 4-hour period.

As discussed below, the subjects were arranged in three histology groups. Within each histologic group, 50% of the subjects received the dosage via the 10 minute IV and the other 50% of the subjects received the dosage over the 4 hour period of time.

Prior to initiating treatment, the tetrasilver tetroxide was subjected a quality assurance protocol to reduce side effects.

Group I: Group I included 10 patients who had been diagnosed as having infiltrative canalicular breast carcinoma.

A 1 cm diameter biopsy fragment was sent to a pathologist laboratory. The pathologist reported an increase of the dense fibrous tissue, anaphasic cells in the gland ducts, forming lines, tubes, ducts, glands and cell anastomosis. The histologic report confirmed the diagnosis of the 10 patients in this group: infiltrative canalicular breast carcinoma.

Group II: Group II included 10 subjects were diagnosed as having ductile carcinoma special type, medular breast cancer.

Group III: Group III included ten patients diagnosed as having infiltrative lobular breast cancer.

For each of the three groups, the dosage was 10 ppm for every subject. The patients had 24-hour evaluations by three oncologists who were each responsible for an 8-hour time period. Every 4 hours, a professional nurse acquired vital signs from the subjects. Twenty-four hour hemodynamic monitoring was performed. The subjects walked 2 hours after they received the dosage and they were prescribed a free diet. Every twenty-four hours, urine was collected. Every seven days, the following laboratory tests were performed: a complete blood count, hemoglobin, hematocracity, vcm, vhcm, complete red blood cells, complete white blood cells, albumin, bilirubin, calcium, and cholesterol, creatine, glucose, ldh, potassium, sodium, triglyceride, uric acid, urea nitrogen, AST and SGOT.

Results of IV Tetrasilver Tetroxide Injection

Group I: Forty-eight hours after treatment, the texture of the nodules had changed from hard as a stone to a mild, soft nodule, the redness was almost gone, and the retraction of the nipple was the same. At 12 days after treatment, the redness was gone, the nodule was no longer discernable by touch, and the nipple retraction had disappeared. Three of the patients who had received 10 minute IV injection exhibited an increase in body temperature and a slight liver enlargement. Liver function was not affected, however, as demonstrated by normal liver function tests, a normal red blood cell count, and a normal white blood cell count. An electrocardiogram did not reveal abnormalities. Sodium, potassium, and magnesium blood levels decreased. Albumin, bilirubin calcium, cholesterol, creatinine, LDH, AST, SGOT, and triglyceride remained normal.

At 19 days after the treatment, the oncologist ordered a new biopsy of this group. The pathologist reported 100% of the biopsies as intralobular ducts normal in number and size. No change in shapes. Cylindric cells in the mammary ducts were normal in shape and in size. Basal membranes were intact. Diagnosis: normal mammary tissue.

After 21 days of treatment, the patients were again evaluated and all of them had tissue retractions in the area where the nodule was located. The subjects had no more symptoms. The patients were allowed to return home after 25 days and given a return appointment in 30 days. The final biopsy revealed no difference between the group that received direct injection and the group that received IV solution. A little quicker response in the IV solution patients was observed in comparison with the direct injection group.

Group II: At 36 hours after treatment, the formerly 10 cm on average tumors had decreased to an average of 8.4 cm and the lymph nodes were smaller and the texture was changed. At day number 16 after treatment, the huge tumor mass was gone, the nodule was no longer palpable, and the lymph enlargement had disappeared. One patient of the sub-group that received direct IV injection exhibited an increase in body temperature and a slight liver enlargement. Liver function was not affected, however, as demonstrated by normal liver function tests, a normal red blood cell count, and a normal white blood cell count. An electrocardiogram did not reveal abnormalities. Sodium, potassium, and magnesium blood levels decreased. Albumin, bilirubin calcium, cholesterol, creatinine, LDH, AST, SGOT, and triglyceride remained normal.

At day number 23 after the treatment, the oncologist ordered a new biopsy of Group II. The biopsy was acquired after 24 days of treatment. The oncologist reported that there were no more hemorrhaging and necrosis zones in the breast tissue. The pathologist reported 90% of the biopsy as intralobular ducts normal in number and size. No change in shape and normal mitosis was observed. Cilindric cells in the mammary ducts were normal in shapes and in sizes and basal membranes were intact. Diagnosis: normal mammary tissue.

Two days later, the patients were evaluated and all of them had tissue retractions in the area where the nodule was located. No more symptoms were exhibited. Six days later, the doctor allowed them to return home with a follow-up appointment scheduled for 30 days. The final biopsy result did not present a difference between the group that received direct injection and the group that received IV solution. A slightly quicker response was observed in the IV solution patients in comparison with the direct injection group.

Group III: At 5 days after treatment, the nipple retraction, bleeding from the nipple, the distorted areola, and the attachment of the mass to surrounding tissues were almost gone. The average nodule size decreased from 4 cm to 2.6 cm. At day number 20 after treatment, the retracted nipples, the bleeding from the nipple, the distorted areola and the attachment of the mass to surrounding tissues was in 90% remission. The average size of the nodules had decreased further from 2.6 cm to 1 cm.

None of the patients of this group that had received direct injection exhibited an increase in the body temperature or even slight liver enlargement. The red blood cells count was normal, and the white blood cells remained normal. The electrocardiogram did not reveal abnormalities. Sodium, potassium, and magnesium blood levels deceased. Albumin, bilirubin calcium, cholesterol, creatinine, LDH, AST, SGOT and triglyceride remained normal.

At day number 29 after the treatment, the oncologist ordered a new biopsy of this group. The pathologist reported 80% of the biopsies as intralobular ducts normal in number and size. No change in shape. Cilindric cells in the mammary ducts normal in shape and in size and the basal membranes were intact. Diagnosis: normal mammary tissue.

Seven days later, the patients were evaluated and all of them had tissue retractions in the area where the nodule was located and did not exhibit any more symptoms. One day later, the patients were allowed to return home and given a follow up appointment in 30 days. The final biopsy result did not indicate a difference between the group that received direct injection and the group that received IV solution. A slightly quicker response was observed, however, for the IV solution patients in comparison with the direct injection group.

Conclusions of IV Tetrasilver Tetroxide Study

1. Tetrasilver tetroxide is preferably delivered in an IV solution to inhibit undesirable side effects.
2. Tetrasilver tetroxide administered by IV appears to stop the growth of the breast cancer.
3. Tetrasilver tetroxide appears to stimulate the normal breast cells and allows them to replace the anaphasic cells in the breast carcinoma.
4. Tetrasilver tetroxide appears to cure infiltrative breast carcinoma in a 24 day period.
5. Tetrasilver tetroxide appears to cure ductile carcinoma special type, medular breast carcinoma in a 30 day period.
6. Tetrasilver tetroxide appears to cure infiltrative lobular breast cancer in a 30 days period.
7. Although certain patients developed mild cases of hepatomegaly, the liver functioning was not impaired as evidenced by the normal levels of liver function enzymes in the blood stream.

Example 2

Treatment of Paget's Disease of the Nipple

A study was performed to determine the affect of the tetrasilver tetroxide compositions of the invention on patients suffering from Paget's disease of the nipple. The compositions were applied in ointment form in this study. Paget's disease of the nipple is a rare type of carcinoma that appears as a unilateral dermatitis of the nipple and represents extension to the epidermis of an underlying mammary duct carcinoma. The redness, oozing, and crusting closely resemble dermatitis, but the physician should suspect carcinoma because the lesion is unilateral.

This study were performed in 25 patients, between 42 to 59 years old. Each patient suffered from Paget's of the nipple, a diagnosis confirmed by biopsy. As discussed below, each patient was placed in one of two groups.

Group 1: Group I included 13 patients with Paget's disease of the nipple, with an average depth of invasion of 0.76 to 1.5 mm. All of the laboratory results indicated the same diagnosis and were taken weekly for 4 weeks. Each patient in this group exhibited metastasis. The lesions were all ulcered and sized on average from 2.3 cm to 3.4 cm. The treatment protocol began with 200 mg of ointment containing 3% tetrasilver tetroxide 3 times per day as applied by a physician. All of the patients were evaluated daily for 4 weeks. None of the patients received anterior treatment.

Group II: Group II included 12 patients suffering from Paget's disease of the nipple, with an average depth of invasion of 2.26 cm to 3.0 cm. All the laboratory results for 4 weeks confirmed the diagnosis. The lesions were all ulcered and sized from an average of 4.3 cm to 5.2 cm. The treatment protocol began with 200 mg of ointment containing 3% tetrasilver tetroxide 3 times per day as applied by a physician. All of the patients were evaluated daily for 4 weeks. None of the patients had anterior treatment.

Results of Paget's Disease Treatment

Group I: Over a period of 15 days, the lesions from Paget's disease began to regress and dry out in all the patients. Pain was gone and the patients began to regain an appetite. The color of the lesions changed from a red more to white. At day 27 of the study, all of the lesions were healed and the lesions were not visible at all. No recurrences of lesions were observed. The last biopsy showed minimum amount of atypical cells, and the mammary ducts were normal.

Group II: Over a period of 23 days the lesions began to regress and became dryer. By the $29^{th}$ day of the study, it was almost impossible to distinguish the lesions. All the patients began to eat normally again and the last biopsy revealed 18% of atypical cells. No recurrences of lesions were found. None of the patients had exhibited side effects.

Conclusions of Paget's Disease Study

The final biopsies, however, revealed 18% atypical cells, suggesting that additional time is required for the tetrasilver tetroxide to completely eliminate the presence of atypical cells.

Example 3

Treatment of Rhabdomyosarcoma with Tetrasilver TetroxideOintment 3%

A study group was formed of twelve patients aged between 45 and 65 years. Each patient had been diagnosed with ulcerative Rhabdomyosarcoma. A pathologist confirmed the diagnosis of each patient based upon a biopsy. All the patients were Caucasian and had similar exposures to sunlight during their lifetimes. All patients had infections demonstrating the presence of pathogens received during chemotherapy and surgical resection treatment. None of the patients exhibited signs of metastasis. As discussed below, the patients were divided into two groups.

Group I: Group I was formed of seven patients with confirmed biopsy diagnosis of ulcerative Rhabdomyosarcoma with extreme infection. Each patient exhibited ulcerative injuries at the inferior member with an extension of 9 cm to 12 cm in diameter. The ulcers exhibited serosanguinous secretions in abundance. The evaluation period began from 4 to 7 months prior to initiating treatment with 3% tetrasilver tetroxide. Each patient started treatment with 200 mg of ointment 3%, three times a day for 30 days.

Group II: Group II was formed of five patients with confirmed biopsy diagnosis of ulcerative Rhabdomyosarcoma with extreme infection. Each case presented extensive ulcerative injuries with indurated edges larger than 12 cm in diameter. The period of evaluation was more than 7 months and all the patients received chemotherapy and surgical resection. Each patient was treated with ointment of 3% of tetrasilver tetroxide of the invention three times a day for thirty days.

Results

Group I: All patients experienced a commencement of healing of the ulcers by day 27 from the start of the treatment. The regions of irritation receded and the color of the lesions became darker and more similar to normal skin color. By day 30, the ulcers were dry and began the scarring process. A biopsy control preformed at the $30^{th}$ day revealed normal muscular tissue with no signs of metaplasia. At the $40^{th}$ day of treatment, a biopsy control was preformed and indicated that the injured metaplastic cells had been replaced by cells of normal appearance. By the $45^{th}$ day, the ulcers were no longer visible. The post-treatment evaluations showed no signs of recidivism.

Group II: All patients showed a commencement of the healing of the ulcers by day 28 from the start of the treatment. By day 40, the ulcers had almost disappeared and a biopsy confirmed that 80% of the diseased tissue had been replaced with healthy tissue. From a clinical standpoint, the ulcers were no longer visible.

The tests demonstrated that the topical application of tetrasilver tetroxide was effective in curing infections and healing skin ulcers associated with Rhabdomyosarcoma, and without significant adverse effects.

Example 4

Topical Treatment with Tetrasilver Tetroxide on Neurofibromatosis

This study was performed to determine the effect of topical treatment with tetrasilver tetroxide on neurofibromatosis. A study group was formed of twelve patients aged 5 months to 3 years who had been diagnosed as having neurofibromatosis. These diagnoses were reconfirmed in conjunction with this study. Diagnoses were made by clinical study and by biopsy of the lesions. None of the patients had received prior treatment. None of the patients exhibited skeletal anomalies or lesions of the optic nerve or acoustic nerve. The patients were arranged in 2 groups as discussed below.

Group I: Group I included eight patients having von Recklinghausen's disease and neurofibromatosis type plexiform neuromas. All of them were symptomatic. The brown spots of the skin were located in the trunk. Each patient applied 200 mg of ointment with 3% tetrasilver tetroxide, 3 times per day for 30 days. Daily evaluations were made to observe progress and to determine the presence of side effects.

Group II: Group II included four patients who had been diagnosed as having von Recklinohausen's disease and neurofibromatosis type neurofibroma. Each diagnosis was confirmed by biopsy. All of the patients were symptomatic. The lesions were located in the trunk, pelvis, and elbows. All of the patients of this group applied 200 mg of ointment with 3% of tetrasilver tetroxide 2 times per day for 30 days. Daily evaluations were made to observe progress and determine the presence of side effects.

Results of Neurofibromatosis Study

Group I: By day 20, five of the eight patients were cured of the spot-type skin lesions. No more symptoms were found. The biopsy result showed normal cells and no reoccurrences were observed. The biopsy results of the other 3 patients showed some atypical cells and the spots, although reduced in color, were still visible.

Group II: At the end of the study, these patients were still symptomatic and the biopsies confirmed the presence of atypical Schwann tumor cells.

Conclusions of Neurofibromatosis Study

Tetrasilver tetroxide ointment seems to have had a positive effect in neurofibromatosis of the plexiform neuromas type. Higher dosages produced a better effect for treatment and management of plexiform neurofibromas.

Tetrasilver tetroxide ointment did not generally seem to produce as thorough a curative result for neurofibroma.

Example 5

Topical Treatment with Tetrasilver Tetroxide on Cervical Carcinoma

In the following examples, the cervical cancer afflictions are divided into two main categories. The first is based on cervical smear (PAP smear) test results following the Bethesda System for reporting cervical cytologic diagnoses bearing designations CIN— the acronym for cervical intraepithelial neoplasia. The second is based on designated NIC stages of which:

0=carcinoma in situ, intraepithelial carcinoma;

1=carcinoma strictly confined to the cervix; and 1A indicates microinvasive carcinoma.

Exetec Lab S.A. located in Honduras, Central America, which performs clinical tests for major pharmaceutical companies did the clinical evaluations of tetrasilver tetroxide on the patients having various cervical cancers. All the clinical testing involved applying 300 mg of an ointment comprising 3% tetrasilver tetroxide dispersed in a hydrocarbon base comprising mostly white petrolatum and mineral oil once a day to the affected cervical/pelvic area.

Five patients classified with CIN 1 cervical cancer, according to cytologic diagnoses were selected. The diagnoses were conducted two months prior to the tetrasilver tetroxide clinical trials. The ointment was applied directly to the cervix and its entrance (endocervix and exocervix) by a skilled physician. The period of administration was tend days per patient. Evaluations were made for any side effects. A biopsy was taken at the end of the treatment. The biopsies indicated that all of the patients were cured without any recurrences.

Five patients who were confirmed as CIN 2, i.e., having high grade squamous intraepithelial lesions including moderate dysplasia 3 months prior to the clinical studies. Two of the patients had familial history of the cervical cancers. This group was treated as outlined by the protocol shown above for 10 days. All patients were cured. The cytologist reported no more atypical cells present and the cytopathologist reported normal cells with no recurrences.

Five patients were confirmed as CIN 3, i.e., having high grade squamous intraepithelial lesions, severe dysplasia and carcinoma in situ one month prior to clinical studies. The ointment was administered to the patients in conformity with the protocol of Example 1 for 10 days. All patients were cured as confirmed by both cytologist and cytopathologist.

Five patients were confirmed as Stage 0 cervical cancer. Three of the patients selected had a familial history of cervical cancer. One patient had a non-bleeding cervical ulcer 1.2×1.5 centimeters. The diagnoses were made 15 days prior to clinical evaluations. The ointment was administered to the patients in conformity with the protocol of Example 1 for 10 days. All patients were cured, including the one with the ulcer, said ulcer healing in 5 days. This was confirmed by both cytologist and cytopathologist with no recurrences.

Five patients were selected who suffered from Stage 1 cervical cancer. Three of the patients had bleeding ulcers. Four had a familial history of cervical cancers. Diagnoses were made 12 days prior to the commencement of clinical trials. The ointment was administered in accordance with the protocol of Example 1 for 15 days. Four out of the five patients were cured. The fifth did not respond. As for the patients with the bleeding ulcers, the ulcers stopped bleeding on the fourth day of the treatment. There were no recurrences in those who were cured.

Five patients with Stage 1A cervical cancer were selected for therapy. Four of the five had bleeding ulcers. Diagnoses were made 3 weeks prior to clinical evaluations. Treatment entailed the protocol of Example 1 over a 20 day period. Three of the patents were completely cured. Those with bleeding ulcers, including the one who was not cured, had all bleeding arrested on the sixth day of therapy. There were no side effects in this group as with all the other groups cited in the previous examples.

All of the 30 patients in these examples were in the age range of 40–60 years old.

Example 6

Treatment of Malignant Melanoma with Tetrasilver Tetroxide

A study group was formed of thirty-one patients between the ages of 48 and 78 years who had been diagnosed with malignant melanomas. The diagnoses were confirmed by biopsy before the study was conducted. The study group included four subgroups as discussed below.

Group I: Group I included fourteen female patients between the ages of 52 to 70 years. Biopsies confirmed superficial spreading melanomas with a depth of invasion ranging from minor to 0.76 mm. The melanomas were located in the interior extremities of the females. Each of the patients began treatment with 200 mg of the 3% tetrasilver tetroxide composition in lotion form applied twice a day. The fourteen patients indicated that they had not previously been treated for the melanoma.

Group II: Group II included eight patients ranging between the ages of 65 to 78 years. A biopsy confirmed the presence of lentigo maligna melanoma. Seven of the eight patients had a depth invasion of 0.76 mm and one of them exhibited a 1.5mm depth of invasion. Each patient was Caucasian and indicated that they had not previously received treatment. Additional laboratory tests demonstrated no pain or secondary effects in the patients. Each of the patients began treatment with 200 mg of the lotion at 3% tetrasilver tetroxide applied three times a day.

Group III: Group III included five patients ranging from ages 60 to 70 years old who had been diagnosed with nodular melanoma. The patients had not previously received treatment. Three of the patients having a depth invasion ranging from minor to 0.76 mm were placed in a subgroup IIIA. Two patients exhibited a depth of invasion ranging 0.51 mm to 2.25 mm and were designated group IIIB. Group IIIB included patients ranging in age from 64 to 68 years old. Two of these patients exhibited discomfort associated with the lungs. Group III initiated treatment with 200 mg of the lotion at 3% tetrasilver tetroxide applied three times per day for 30 days.

Group IV: Group IV included four patients between the ages of 45 to 54 years old who had been diagnosed with acrolentiginous melanoma. Two of the patients had received prior treatment with no success. The depth invasion ranged between 1.51 to 2.25 mm. These two patients were designated Group IVA. The remaining patients, Group IVB, exhibited a depth of invasion ranging from minor to 0.76 mm. No discomfort was reported by Group IV patients. Group IV began treatment with 200 mg of the lotion at 3% tetrasilver tetroxide applied three times per day for thirty days.

Results of the Melanoma Study

Each patient from Group I exhibited improvement by the sixth day of treatment. The dark blue spots were losing color. By the eighth day of treatment, the border on the injuries indicated improvement. By the fourteenth day of treatment, none of the injuries exhibited inflammation. On the fifteenth day of treatment, a biopsy was conducted, which indicated that the malignant melanomas had been replaced by normal epidermis while the dermis showed a decrease in the malignant melanomas compared to the first biopsy. By day 22, the blue spots had disappeared completely and the borders of the spots were not visible at all. A new biopsy was conducted at the thirtieth day of treatment, which showed the absence of the malignant melanomas from both the dermis and epidermis.

The eight patients of Group II exhibited improvement by the eighth day of treatment. The melanomas of the dermis had changed from black and/or dark brown to a lighter color. By the fourth day, the injuries had disappeared. At the fifth day, a new biopsy was conducted. The biopsy indicated that the ratio of malignant melanomas to normal melanocytes, i.e., benign melanomas, had decreased in relation to the pre-study biopsy. The patients observed that the injuries had disappeared and healed. A biopsy conducted at the twentieth day of treatment indicated normal melanocytes. The patients have been monitored without any changes from the above described results.

The patients of Group IIIA observed that their injuries had begun to heal between the 9th and 10th day of the treatment. By the fourteenth day of treatment, the grey colored spots were no longer visible. At the sixteenth day of treatment, a new biopsy was obtained showing just a few malignant melanomas and the appearing of normal melanocytes. By the twenty-sixth day, the injuries were hardly visible, appearing only as small scars. A biopsy obtained at the thirtieth day indicated the presence of only normal melanocytes.

The patients of group IIIB exhibited few changes by the twenty-second day of treatment. A biopsy obtained at the twenty-fifth day of treatment indicated the presence of malignant melanomas. No significant changes were reported at the thirtieth day. A biopsy obtained at the this time indicated the presence of malignant melanomas and minimum inflamation characteristics.

The patients of group IVA exhibited no change by the thirtieth day of the treatment. A biopsy obtained at the this time indicated the presence of malignant melanomas. The patients of group IVB, however, exhibited changes to the border and color of the injuries by the second day of treatment. By the sixth day of treatment, the injuries were not visible and a biopsy acquired at the fifteenth day indicated normal melanocytes.

Conclusions of the Melanoma Study

The present compositions, in ointment form, healed superficial spreading melanomas within 8 to 14 days of treatment when the depth of invasion was less than 0.76 mm. The biopsies indicated that the cancer was eliminated. The compositions healed the lentigo-maligna having an invasion depth between 0.76 mm to 1.5 mm. No discomfort or side effects reported. The compositions also eliminated nodular melanoma with a depth invasion of 0.76 mm or less within a sixteen day treatment period. The compositions did not eliminate the nodular melanoma having a metastasis condition with a depth of invasion of 1.51 mm to 2.25 mm within thirty days in this study.

The compositions of the invention were highly effective at treating the acrolentiginous melanoma condition with a depth invasion ranging from minor to 0.76 mm (without metastasis). The compositions eliminated the cancer in 100% of these cases. The present compositions were an effective treatment for the melanomas where chemotherapy and surgical resources were ineffective. The compositions did not, however, have a noticeable effect upon acrolentiginous melanoma with a depth of invasion ranging from 1.5 mm to 2.25 mm within a period of 30 days of treatment.

Example 7

Preparation of a 3% Tetrasilver Tetroxide Ointment

A paraffinic hydrocarbon ointment was prepared by heating with agitation a mixture comprising about 33 wt % heavy mineral oil and about 67 wt % of petroleum jelly to a temperature of 70° C. and then dispersing in this mixture the finely divided tetrasilver tetroxide powder sufficient to provide a 3% by weight concentration of the oxide in the carrier. The mixture was then cooled to room temperature with continuous stirring until the mixture was no longer liquefied. It should be understood that the methods of this example can be used in preparing the ointments and lotions of Examples 1–6, as well as other compositions according to the invention, as will be readily understood by those of ordinary skill in the art.

Example 8

Treatment of Melanoma

A male age 47 was diagnosed as having melanoma at least for three years. He exhibited at least 15 blotchy brown lesions scattered on both forearms. The size of the affected areas varied from 0.3 mm to 1.2 mm. The ointment of Example 7 was applied to the affected skin areas of the arms at least once a day. After one week, the brown blotches had been modified or replaced by pink ones. After 2 weeks, the pink areas were gone. After 3 and 4 weeks, there was no evidence of any melanoma.

Example 9

Treatment of Basal Cell Carcinoma

Two patients, one a male age 83 and the other a female age 63, were treated in the same manner as in Example 8 for basal cell carcinoma. The female had one large brown cancer growth varying from 0.6–1.4 mm by 0.9–3.6 mm on top of the scalp. The male had several white head pimples 0.3–0.7 mm. One was on the right ear. Five were on the scalp and another was on the left leg. After one week the female observed that her tumor had diminished to just a minor pink skin irritation. After two weeks, the pink irritation had vanished. After four weeks had elapsed, the skin was clear and normal in appearance. As for the male, after one week all white head pimples had regressed to a pink inflammation except for the ear, which appeared to be completely healed. After the second week, all pink areas were gone, as well as any indications of inflammation. After the third and fourth weeks, all previously afflicted areas showed no evidence of basal cell carcinoma.

Example 10

Treatment of Squamous Cell Carcinoma

A male patient, age 74, was afflicted with squamous cell carcinoma. The sores were on both arms, with five on the right and seven on the left. Their appearance was oval shaped ranging from 2.5–5.5 mm in length. This patient was treated in the same manner as in Example 8 by applying the ointment of Example 7 to the affected skin areas. After one week of treatment, all open sores had closed and were in the process of healing. During the second week, sores continued to heal at a rapid pace. Scabs were completely gone by the end of the second week. At the end of the third week, only slight pink areas remained in the place of the previous sores. By the end of the fourth week, there were no traces of the previous affliction.

Example 11

Treatment of Basal Cell Carcinoma with Tetrasilver Tetroxide Ointment 3%

This study included twenty patients ranging in age from 45 to 65 years old, all of whom had been diagnosed with basal cell carcinoma. The diagnoses were confirmed by a pathologist via biopsy. All the patients were Caucasian and commonly experienced a similar exposure level to sunlight during their lives.

Group I: Group I included ten patients exhibiting injuries of less then 1 cm in size with nodules that were bright and ulcerated. At the time of diagnosis, no form of treatment had been implemented. The patients had been evaluated for one month prior to treatment with tetrasilver tetroxide composition of the invention formulated as an ointment of 3% tetrasilver tetroxide. Each of the affected areas was located in a region of the body exposed to sunlight. Each patient began treatment with 200 mg tetrasilver tetroxide ointment 3%, three times a day for thirty days.

Group II: Group II was formed by 10 patients having injuries larger than 1 cm. The injuries were clinically present as nodules that were ulcerated and with indurated edges. In each case, the period of evaluation exceeded one month. Each patient began treatment with 200 mg tetrasilver tetroxide ointment 3%, three times a day for 30 days.

Results

Group I: Each patient within this group displayed a healing process of the ulcerated nodules by the seventh day of treatment. It was no longer possible to visualize the irritations and the bright color became darker and more similar to the normal skin. By the twelfth day of treatment, the ulcers were not visible at all and the scarring process had begun. Controlled biopsies taken at the fifteenth day of treatment indicated that the metaplastic cells from the injuries had been replaced by normal appearing cells. The nodules were smaller than 0.5 cm. By the twenty-fourth day of treatment, the nodules were not visible and only showed a light zone of papular tissue. The biopsy control performed at 30 days revealed normal basal cellular tissue with no signs of metaplastic cells. No recidivism was observed at the thirty day examination.

Group II: Each patient in this group exhibited changes in the nodules up to the fifteenth day of treatment when the beginning of the drying process began and the nodules stopped exhibiting signs of peripheral irritation areas. Biopsies performed on the 16th day of treatment indicated a reduction in metaplastic cell with newly formed cells. The ration of metaplastic cells to the normal cells began to invert by the thirtieth day of treatment, and the ulcerated nodules had disappeared and were only indicated by a few light zones. Biopsies performed on the thirtieth day revealed that 80% of the affected tissue was occupied by normal basal cells, but also indicated the presence of metaplastic cells. The post-treatment evaluation at 30 days did not clinically indicate any of the previous skin injuries.

In general, the results of the Group I and Group II studies indicate that tetrasilver tetroxide ointment 3% was effective in the treatment of basal cell carcinoma on injuries both smaller and larger than 1 cm. The results, however, indicated that in the treatment of basal cell carcinoma, it is most important to obtain and begin treatment as rapidly as possible. Treatment was most effective the earlier the time of diagnosis.

Example 12

Treatment of Dysplastic Nevi According to the Invention

Ten patients between the ages of 25 to 40 were clinically diagnosed by biopsy with dysplastic nevi. The patients were divided into two groups.

Group I had six patients with dermal injuries of 5 to 10 mm.

Group II had four patients with dermal injuries of more than 12 mm. The illness was well developed on the skin.

A petroleum jelly containing 3 wt % tetrasilver tetroxide was applied to both groups at a dosage of about 100 mg to all affected skin areas of each patient twice daily. Observations of both groups were made for a 30 day period to ensure there were no additional changes in the condition.

Summary of Results

Group I: Within 36 hours of the onset of treatment, the color and size of the injuries began to change, i.e., turn into smaller spots. By the sixth day, the dysplastic nevi were no longer visible. By the eighth day, a biopsy was conducted revealing new normal melanocytes. The patients were evaluated for the duration of the period, with no further changes reported.

Group II: By the fourth day of treatment, changes had started to occur. The color from the spots had started to disappear, and they were also turning smaller. By the fifteenth day, a new biopsy was taken showing normal melanocytes, with the injuries no longer visible. Patients did not experience any further changes in their condition over the 30 days.

In conclusion, it is believed that early diagnosis resulted in better and faster treatment results according to the invention, with no significant adverse effects reported. Also, the larger the injuries, the longer the treatment time required. The above test also showed that the tetrasilver tetroxide treatment was effective to prevent the malignant melanoma, since 90% of them derive from dysplastic nevi.

Example 13

Cytotoxicity Tumor Cell Proliferation Studies and Evaluations

An independent laboratory performed cytotoxicity tumor cell proliferation studies and evaluations. A culture of leukemia K562 was tested in vitro against media concentrations of tetrasilver tetroxide at: 0.5, 1,5, 10, 50, 100, 500 and 1000 ppm.

The tetroxide was dispersed in pure dimethyl sulfoxide and then diluted with Holipharm NPS buffer PH=7.4 (Holipharm International Co., Wilmington, Del.) in culture media to achieve the aforesaid final assay concentrations. The acronym NPS refers to non phosphate non saline. The culture media comprised RPMI 1640, 90% and fetal bovine serum, 10%. The cancer cultures were obtained from a cell line provided by the American Type Culture Collection (ATCC) and were incubated at 37° C. with 5% $CO_2$ in air atmosphere. The culture was a human chronic myelogenous leukemia, of cell line source ATCCCCL-243.

As for the actual evaluation, cell proliferation analysis was based on the ability of viable cells to cause alamar blue to change from oxidized (non-fluorescent, blue) to reduced (fluorescent, red) form. Details of the procedure are described in an article by S. Ansar Ahmed et. al. in the Journal of Immunological Methods 170 (1994). The results were as follows:

$IC_{50}$ (50% Inhibition Concentration)=2.2 ppm
TGI (Total Growth Inhibition)=4.6 ppm
$LC_{50}$ (50% Lethal Concentration)=6.0 ppm The above methodology was applied to a human malignant melanoma cell line of source ATCCHTB-70 having the cell name SK-MEL-5. The culture media comprised 90% Minimum Essential Medium and fetal bovine serum, 10%. The results were as follows:

$IC_{50}$ (50% Inhibition Concentration)=3.7 ppm
TGI (Total Growth Inhibition)=4.9 ppm
$LC_{50}$ (50% Lethal Concentration)=6.5 ppm The $^aIC_{50}$ (50% Inhibition Concentration) is the test compound concentration where the increase from times in the number or mass of treated cells was only 50% as much as the corresponding increase in the vehicle-control at the end of experiment. The bTGI (Total Growth Inhibition) is the test compound concentration where the number or mass of treated cells at the end of experiment was equal to that at time. The CLC (50% Lethal Concentration) is the test compound concentration where the number or mass of treated cells at the end of experiment was half that at time. Table 1.1 shows other results from this study.

Although preferred embodiments of the invention have been illustrated in the foregoing Summary, Detailed Description, and Examples, it will be understood that the invention is not limited to the embodiments disclosed, but is capable of numerous rearrangements and modifications of parts and elements without departing from the spirit of the invention. It will be further understood that the chemical and pharmaceutical details of the compositions and methods of prevention, treatment, or management herein may be slightly different or modified by one of ordinary skill in the art without departing from the claimed invention.

What is claimed is:

1. A method for preventing, treating, or managing one or more cancerous conditions or dysplastic proliferations in an animal, which method comprises:
    administering at least one metal oxide compound selected from the group consisting of Bi(III,V) oxide, Co(II,III) oxide, Cu(I,III) oxide, Mn(II,III) oxide, Pr(III,IV) oxide, and Ag(I,III) oxide to the animal in an amount and for a period of time which is therapeutically effective to treat such condition(s).

2. The method of claim 1, wherein the metal oxide compound is administered via intravenous injection or infusion and the animal is a human.

3. The method of claim 2, wherein the administering is subcutaneous, intramuscular, or by infusion into a blood stream of the animal.

4. The method of claim 3, wherein the metal oxide compound is administered via infusion over a period of from about 30 minutes to about 300 minutes to inhibit adverse side effects.

5. The method of claim 4, wherein the at least one other chemotherapeutic agent is administered concurrently with the metal oxide compound.

6. The method of claim 2, wherein the cancer includes skin cancer that has metastasized.

7. The method of claim 1, wherein the metal oxide compound is administered via intravenous injection or infusion and the animal is a human.

8. The method of claim 7, wherein the metal oxide compound is administered in an amount sufficient to provide about 1 to about 75 ppm of the metal oxide compound in the bloodstream.

9. The method of claim 1, wherein the metal oxide compound is administered in conjunction with at least one other chemotherapeutic agent.

10. The method of claim 1, wherein the cancerous condition or dysplastic proliferation includes at least one of colon cancer, lung cancer, throat cancer, breast cancer, kidney cancer, pancreatic cancer, bladder cancer, prostate cancer, uterine cancer, brain cancer, liver cancer, skin cancer, testicular cancer, stomach cancer, adrenal gland cancer, cancer of the ovaries, thyroid cancer, bronchial cancer, trachea cancer, eye cancer, bone cancer, cervical cancer, oral cavity cancer, soft tissue cancer, pituitary gland cancer, myeloma, rectal cancer, esophageal cancer, leukemia, lymphoma, cancerous fibroid tumors, non-cancerous fibroid tumors, or liver cancer.

11. The method of claim 10, wherein the controlled release vehicle is implanted in the body at a location suitable for providing a therapeutically effective amount of metal oxide compound to the patient without affecting proper functioning of the animal's liver.

12. The method of claim 1, wherein the metal oxide compound is administered by a controlled release vehicle.

13. The method of claim 1, wherein the metal oxide compound is substantially free of added persulfate.

14. A method for preventing, treating, or managing one or more cancerous conditions or dysplastic proliferations associated with a patient's skin, which method comprises administering the at least one metal oxide compound selected from the group consisting of Bi(III,V) oxide, Co(II,III) oxide, Cu(I,III) oxide, Mn(II,III) oxide, Pr(III,IV) oxide, and Ag(I, III) oxide to the skin in an amount and for a period of time which is therapeutically effective to treat such cancerous condition(s).

15. The method of claim 14, wherein the at least one metal oxide compound is substantially free of added persulfate.

16. The method of claim 14, wherein the cancerous condition or dysplastic proliferation comprises at least one of dysplastic nevi, neurofibromatosis, basal cell carcinoma, squamous carcinoma, or melanoma.

17. The method of claim 14, wherein the cancerous condition or dysplastic proliferation comprises symptoms of cancer or conditions associated with a predisposition to cancer.

18. The method of claim 14, further comprising a carrier medium in which the at least one metal oxide compound is dispersed, wherein the therapeutically effective amount is from about 50 ppm to 500,000 ppm, based on the weight of the carrier medium.

19. The method of claim 18, wherein the carrier medium comprises petroleum jelly or mineral oil.

20. The method of claim 14, wherein the at least one metal oxide compound is administered in the form of a powder.

21. The method of claim 14, wherein the therapeutically effective amount is from about 400 ppm to 100,000 ppm.

22. The method of claim 14, wherein the administering is topical or transdermal.

23. The method of claim 22, wherein the composition is topically administered directly to the skin.

24. The method of claim 23, wherein the at least one metal oxide compound further comprises a thixotropic agent sufficient to increase adherence of the composition to the skin without excessive runoff.

25. The method of claim 14, wherein the administering comprises application of the at least one metal oxide to the skin at a dosage level of about 10 mg to 500 mg per $cm^2$ of skin surface.

26. A method for preventing, treating, or managing one or more cancerous conditions associated with a cervix of a female animal, which method comprises administering at least one metal oxide compound selected from the group consisting of Bi(III,V) oxide, Co(II,III) oxide, Cu(I,III) oxide, Mn(III,II) oxide, Pr(III,IV) oxide, and Ag(I,III) oxide to the cervix in an amount and for a period of time which is therapeutically effective to treat such condition(s).

27. The method of claim 26, wherein the at least one metal oxide compound is substantially free of added persulfate.

28. The method of claim 27, wherein the at least one metal oxide compound is applied directly to the cervix.

29. The method of claim 28, further comprising a carrier medium in which the at least one metal oxide compound is dispersed, wherein the therapeutically effective amount is from about 50 ppm to 500,000 ppm, based on the weight of the carrier medium.

30. The method of claim 29, wherein the carrier medium comprises petroleum jelly.

31. The method of claim 26, wherein the at least one metal oxide compound is applied in an amount sufficient to obtain a desired effect and to substantially inhibit undesirable side effects.

* * * * *